(12) United States Patent
Arbefeuille (10) Patent No.: US 8,702,787 B2
(45) Date of Patent: *Apr. 22, 2014

(54) ENDOLUMINAL PROSTHESIS

(75) Inventor: Samuel Arbefeuille, Hollywood, FL (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1461 days.

This patent is subject to a terminal disclaimer.

(21) Appl. No.: 11/218,917

(22) Filed: Sep. 2, 2005

(65) Prior Publication Data

US 2007/0055347 A1 Mar. 8, 2007

(51) Int. Cl.
*A61F 2/06* (2013.01)

(52) U.S. Cl.
USPC .......................................................... 623/1.15

(58) Field of Classification Search
USPC .............. 623/1.11–1.15, 1, 12; 606/192, 194, 606/198
See application file for complete search history.

(56) References Cited

U.S. PATENT DOCUMENTS

| | | | |
|---|---|---|---|
| 5,217,483 A | 6/1993 | Tower | |
| 5,282,824 A * | 2/1994 | Gianturco | 623/1.13 |
| 5,545,211 A | 8/1996 | An et al. | |
| 5,665,115 A | 9/1997 | Cragg | |
| 5,713,917 A | 2/1998 | Leonhardt et al. | |
| 5,824,041 A | 10/1998 | Lenker et al. | |
| 6,524,335 B1 * | 2/2003 | Hartley et al. | 623/1.13 |
| 2002/0156523 A1 * | 10/2002 | Lau et al. | 623/1.13 |
| 2002/0177890 A1 * | 11/2002 | Lenker | 623/1.12 |
| 2003/0088305 A1 * | 5/2003 | Van Schie et al. | 623/1.12 |
| 2004/0082989 A1 * | 4/2004 | Cook et al. | 623/1.13 |
| 2004/0215319 A1 | 10/2004 | Berra et al. | |

FOREIGN PATENT DOCUMENTS

| | | | |
|---|---|---|---|
| EP | 0832618 | 4/1998 | |
| EP | 1029517 | 8/2000 | |
| WO | WO 95/26695 | 10/1995 | |
| WO | WO 96/39999 | 12/1996 | |
| WO | WO 01/19286 | 3/2001 | |
| WO | WO 01/39696 | 6/2001 | |
| WO | WO 01/39696 A1 * | 6/2001 | ............... A61F 2/06 |
| WO | WO 01/58386 | 8/2001 | |

* cited by examiner

*Primary Examiner* — S. Thomas Hughes
*Assistant Examiner* — Julie A Szpira (57) ABSTRACT

An endoluminal prosthesis is provided that includes a tubular graft and an expandable annular support structure. The annular support structure is coupled to the tubular graft so that the graft and support structure, in combination, provide columnar support while maintaining prosthesis flexibility. The prosthesis has sufficient strength and durability to withstand loads applied during deployment and sufficient flexibility to permit implant in a sealing arrangement within a tortuous body lumen. An embodiment according to the invention provides a plurality of annular structures with staggered, longitudinally overlapping apices of undulating structures. One embodiment relates to tubular grafts for endoluminal placement within a body lumen, including blood vessels, and for the treatment of abdominal and other aneurysms.

17 Claims, 8 Drawing Sheets

ENDOLUMINAL PROSTHESIS

FIELD OF THE INVENTION

The present invention relates to tubular prostheses such as grafts and endoluminal prostheses including, for example, stent-grafts and aneurysm exclusion devices, and methods for placement of such grafts and endoluminal structures. More particularly, the present invention relates to an improved a tubular graft and support structure for placement within or in place of a body lumen.

BACKGROUND OF THE INVENTION

A wide range of medical treatments have been previously developed using "endoluminal prostheses," which terms are herein intended to mean medical devices which are adapted for temporary or permanent implantation within a body lumen, including both naturally occurring or artificially made lumens. Examples of lumens in which endoluminal prostheses may be implanted include, without limitation: arteries such as those located within coronary, mesentery, peripheral, or cerebral vasculature; veins; gastrointestinal tract; biliary tract; urethra; trachea; hepatic shunts; and fallopian tubes. Various types of endoluminal prostheses have also been developed, each providing a uniquely beneficial structure to modify the mechanics of the targeted luminal wall.

A number of vascular devices have been developed for replacing, supplementing or excluding portions of blood vessels. These vascular grafts may include but are not limited to endoluminal vascular prostheses and stent grafts, for example, aneurysm exclusion devices such as abdominal aortic aneurysm ("AAA") devices that are used to exclude aneurysms and provide a prosthetic lumen for the flow of blood.

One very significant use for endoluminal or vascular prostheses is in treating aneurysms. Vascular aneurysms are the result of abnormal dilation of a blood vessel, usually resulting from disease or a genetic predisposition which can weaken the arterial wall and allow it to expand. While aneurysms can occur in any blood vessel, most occur in the aorta and peripheral arteries, with the majority of aneurysms occurring in the abdominal aorta. Typically an abdominal aneurysm will begin below the renal arteries and may extend into one or both of the iliac arteries.

Aneurysms, especially abdominal aortic aneurysms, have been most commonly treated in open surgery procedures where the diseased vessel segment is bypassed and repaired with an artificial vascular graft. While considered to be an effective surgical technique in view of the alternative of a fatal ruptured abdominal aortic aneurysm, the open surgical technique suffers from a number of disadvantages. The surgical procedure is complex and requires long hospital stays due to serious complications and long recovery times and has high mortality rates. In order to reduce the mortality rates, complications and duration of hospital stays, less invasive devices and techniques have been developed. The improved devices include tubular prostheses that provide a lumen or lumens for blood flow while excluding blood flow to the aneurysm site. They are introduced into the blood vessel using a catheter in a less or minimally invasive technique. Although frequently referred to as stent-grafts, these devices differ from covered stents in that they are not used to mechanically prop open natural blood vessels. Rather, they are used to secure an artificial lumen in a sealing engagement with the vessel wall without further opening the natural blood vessel that is already abnormally dilated.

Typically these endoluminal prostheses or stent grafts are constructed of graft materials such as woven polymer materials (e.g., Dacron) or polytetrafluoroethylene ("PTFE") and a support structure. The stent-grafts typically have graft material secured onto the inner diameter or outer diameter of a support structure that supports the graft material and/or holds it in place against a luminal wall. The prostheses are typically secured to a vessel wall above and below the aneurysm site with at least one attached expandable annular spring member that provides sufficient radial force so that the prosthesis engages the inner lumen wall of the body lumen to seal the prosthetic lumen from the aneurysm. In some devices, a radially expandable member partially extends proximally in an axial direction from the graft material. The ring member is substantially uncovered, i.e., has openings through which blood may flow and is therefore useful in placing the device at or near the junction of other vasculature, e.g., at or near the renal artery where a stent graft is being used to exclude an abdominal aortic aneurysm. When the expandable member must be placed near the renal artery, for example, such an axially extending ring member may be used so that blood may flow through openings in the expandable member so that the renal arteries are not occluded. In other devices, other mechanisms have also been used to engage the vessel walls such as, for example, forcibly expandable members or hook like members that puncture the vessel wall. In some devices where attached expandable ring members are used, a support bar attaches the ring members to provide columnar support along the length of the bar.

One of the characteristics desired to prevent collapse of the stent graft is columnar strength. However, the features that provide columnar strength may also reduce device flexibility that permits sealing placement of the device within a tortuous vessel, such as, e.g., a diseased iliac vessel. Further, the devices are subject to cyclical loading and other stresses. Accordingly it would be desirable to provide a device structure having desired loading characteristics, with sufficient columnar strength, while maintaining sufficient flexibility to allow placement and sealing of the prosthesis within a tortuous vessel.

Additionally, to provide catheter access to the site and make it maneuverable through the tortuous or narrowed diseased vessels, it is desirable to provide a stent graft with a high degree of radial compressibility. Therefore, it is desirable to provide an endoluminal tubular graft that has sufficient strength and loading characteristics while maintaining flexibility and radial compressibility into for delivery from a relatively small diameter delivery catheter.

Further, it is important for the aneurysm exclusion device to sufficiently seal against the vessel wall to prevent blood from entering the aneurysm site as it flows through the artificial lumen. Accordingly, it would be desirable to provide an improved seal, especially at the proximal end of the prosthesis.

SUMMARY OF THE INVENTION

An embodiment according to the present invention provides an improved endoluminal prosthesis having a tubular graft and a support structure attached to the tubular graft and configured in a manner that provides columnar strength while providing improved device flexibility, and a maintaining a relatively small pre-deployed, collapsed profile.

An embodiment of the endoluminal prosthesis comprises a tubular member constructed of a graft material and at least one annular support member. The tubular graft is formed of a woven polymer fiber for conducting fluid. The tubular member includes, a proximal opening and a distal opening providing a lumen through which body fluids may flow. The annular support members support the tubular graft and/or maintain the lumen in a conformed, sealing arrangement with the inner wall of a body lumen.

The annular support members each comprise an annular expandable member formed by an undulating or sinusoidal patterned wire ring. The pattern is formed by a plurality of straight spokes connected by a plurality of apices (alternating crests and troughs) to form a closed ring with an axis extending longitudinally therethrough. Preferably the annular support members are radially compressible springs biased in a radially outward direction, which when released, bias the prosthesis into conforming fixed engagement with an interior surface of the vessel. Annular springs are provided particularly where the annular support member is used to create a seal between the prosthesis and the inner wall of a body lumen. The annular springs are preferably constructed of Nitinol. Examples of such spring means construction are described, for example, in U.S. Pat. Nos. 5,713,917 and 5,824,041 incorporated herein by reference. When used in an aneurysm exclusion device, the spring has sufficient radial spring force and flexibility to conformingly engage the prosthesis with the body lumen inner wall, to avoid excessive leakage, and prevent pressurization of the aneurysm, i.e., to provide a leak resistant seal. Although some leakage of blood or other body fluid may occur into the aneurysm isolated by the prosthesis, an optimal seal will reduce the chances of aneurysm pressurization and resulting rupture.

The annular support members are attached or mechanically coupled to the graft material along the tubular graft by attaching overlapping adjacent apices of adjacent support members within the circumferential areas defined by the support member. The support member may be attached to the graft by various means, such as, for example, by stitching onto either the inside or outside of the tubular graft. Each of the support members defines a corresponding circumferential area of graft material around it. In one embodiment, at least one of the apices of an annular support member is mechanically coupled to the circumferential graft area of an adjacent annular support member. In an embodiment according to the invention, at least one of the apices of the annular support member of the invention extends axially beyond the other apices of that annular support member. In this embodiment, the longer crest(s) and/or trough(s) extend into and are attached to the circumferential graft area of an adjacent annular member. The overlap on the graft thus provides columnar strength along the length of the graft from one support structure through the graft and to the next support structure. The overlapping structure also prevents collapse of the graft between support structures. Further, providing fewer overlapping structures allows greater radial compressibility of the prosthesis.

In one embodiment according to the invention, the apices, or crests and troughs of at least one support structure overlap lengthwise (i.e., with respect to the length or axis of the prosthesis) an apex of an adjacent support structure. Such an apex is offset from adjacent apices of the adjacent support structure about the circumferential area of the adjacent support structure. The troughs of a support structure are staggered about the circumference from the crests of an adjacent support structure so that the support structures do not physically touch. In one embodiment, longer crests or longer troughs of each of the support members are substantially aligned with the other longer crests or longer troughs of adjacent support structures, respectively, to provide column strength along a desired length of the prosthesis.

In one embodiment, the support structure is formed of a series of connected M-shaped patterns where the troughs are alternatingly long and short. An adjacent support structure is formed of a series of alternating upside down M-shaped patterns where the peaks are alternatingly long and short. The longer troughs of the first support structure are generally axially aligned with the shorter peaks of the adjacent support structure while the shorter troughs of the first support structure are generally axially aligned with the longer peaks of the adjacent support structure. The adjacent longer troughs and longer crests of support structures adjacent to each other are thus staggered circumferentially from each other so that the adjacent longer troughs of a first annular support structure do not physically overlap with the adjacent longer crests of an adjacent second annular support structure.

An embodiment according to the present invention provides such a tubular graft and improved support structure for endoluminal placement within a blood vessel for the treatment of abdominal and other aneurysms. In this embodiment, the endoluminal prosthesis is an aneurysm exclusion device forming a lumen for the flow of body fluids excluding the flow at the aneurysm site. The aneurysm exclusion device may be used for example, to exclude an aneurysm in the aorta, such as in the abdominal aorta or in the thoracic region. In an abdominal aorta, the prosthesis may be bifurcated.

The present invention in the embodiment of an Abdominal Aortic Aneurysm ("AAA") device, the prosthesis is able withstand the loads applied during deployment and the cyclical loading in the body for a reasonable duration and provides sealing attachment of the annular support structure to the inner wall of the body lumen.

Another aspect of the invention provides an annular support member with sealing points at multiple levels or different heights around the proximal portion of the prosthesis with or without longitudinal overlap. The annular support member sewn on to the tubular graft, comprises an undulating or sinusoidal patterned wire ring. The pattern is formed by a plurality of straight spokes connected by a plurality of apices (alternating crests and troughs) to form a closed ring with an axis extending longitudinally therethrough. The crests are preferably coupled to the proximal end of the graft material while the troughs are provided having several different lengths with respect to the axis of the support member, or the length of the tubular graft. Thus in addition to radially biasing the edge of the fabric and equidistant points below the edge, multiple levels for radially biased sealing points are provided. This is particularly useful in providing greater device conformity with the inner wall of a lumen while maintaining a relatively low device profile when it is radially compressed for delivery. One embodiment according to this aspect of the invention is a support structure is formed of a series of connected M-shaped patterns where the troughs are alternatingly long and short. An adjacent support structure may, for example, be formed of a series of alternating upside down M-shaped patterns where the peaks are alternatingly long and short, with the longer troughs of the first support structure generally axially aligned with the shorter peaks of the adjacent support structure and the shorter troughs of the first support structure generally axially aligned with the longer peaks of the adjacent support structure. Alternatively the M shaped patterns may be right side up or a combination of upside down and right side up.

The endoluminal prosthesis may be in the form of either a straight single-limb tubular member or a generally Y-shaped bifurcated tubular member having a trunk joining at a graft junction with a pair of lateral limbs, namely an ipsilateral limb and a contralateral limb. In a bifurcated prosthesis, the proximal portion of the prosthesis comprises a trunk with a proximal opening and the distal portion is branched into at least two branches with distal openings. Thus body fluids may flow from the proximal opening through the distal openings of the branches. Preferably the ipsilateral limb is longer so that when deployed, it extends into the common iliac. A single limb extension member is provided having a mating portion for engaging and sealing with a lateral limb of a bifurcated member and a leg (whose length may vary as selected to mate with a particular patient's anatomy) extending coaxially from a distal end of the mating portion. In one embodiment according to the invention, the improved annular support members are located on the proximal portion of the prosthesis. In another embodiment according to the invention, the annular support members are located on at least one of the iliac portions to provide increased flexibility when deployed in a tortuous vessel.

The compressed profile of the prosthesis is sufficiently low to allow the endoluminal graft to be placed into the vasculature using a low profile delivery catheter. The prosthesis can be placed within a diseased vessel via deployment means at the location of an aneurysm. Various means for deployment of the devices are well known in the art and may be found for example is U.S. Pat. Nos. 5,713,917 and 5,824,041, which are incorporated herein by reference. In general, the endoluminal prosthesis is radially compressed and loaded into a catheter. The aneurysm site is located using an imaging technique such as fluoroscopy and is guided through a femoral iliac artery with the use of a guide wire to the aneurysm site. Once appropriately located, the sheath on the catheter covering the tubular graft is retracted, thus allowing the annular springs to expand and attach or engage the tubular member to the inner wall of the body lumen. The iliac extension is also loaded into a catheter and is then located into the main body of the stent graft and within the iliac vessel where it is deployed. When deployed, the iliac extension is engaged using annular springs proximally within the inner lumen of the main body and distally with the inner wall of the iliac vessel.

These and further aspects of the invention are exemplified and in the detailed description of embodiments according to the invention described below.

BRIEF DESCRIPTION OF THE DRAWINGS

FIG. 6C is the enlarged portion of FIG. 6B in which
FIG. 6D is the enlarged portion of FIG. 6B in which
FIG. 6E is the enlarged portion of FIG. 6B in which
FIG. 6F is the enlarged portion of FIG. 6B in which

DETAILED DESCRIPTION

FIGS. 1-8B illustrate various embodiments of the support structures and endoluminal prostheses according to the present invention. Although an endoluminal prosthesis according to the invention may be used in any body lumen that conducts body fluid, it is described herein with reference to treatment of an aortic aneurysm, in particular in the abdomen of a patient.

Figure 1:
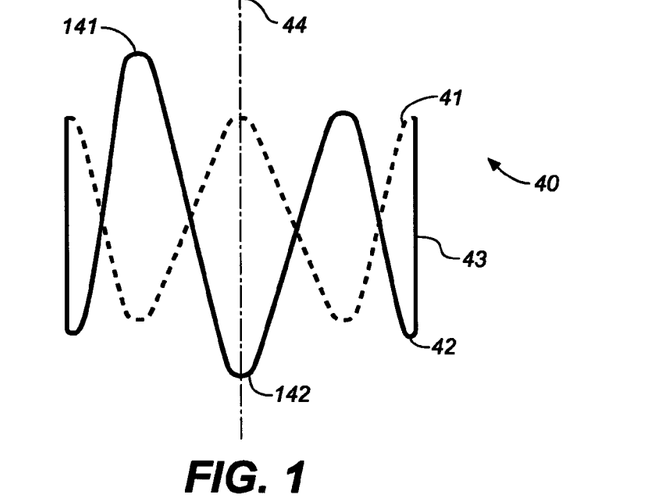
FIG. 1 is an elevational perspective view of a first embodiment of an annular support member of a support structure of an endoluminal prosthesis according to an embodiment of the invention.

FIG. 1 illustrates a first embodiment of an annular support member 40 used in an endoluminal prosthesis of an embodiment according to the invention. The annular member 40 comprises five connected V-shaped patterns in a cylindrical undulating ring (undulating member or straight spokes coupled at apices). In forming this pattern, the annular member 40 comprises straight spokes 43 connected by rounded alternating crests 41 and troughs 42 encircling a central axis 44 to provide a continuous ring. Of the crests 41 and troughs 42 there is at least one longer crest 141 and at least one adjacent longer trough 142, each formed so that the longer crest 141 and longer trough 142 extend a greater distance axially from the middle circumference 45 (FIG. 2) of the annular member 40, than the other crests 41 and troughs 42.

Figure 2:
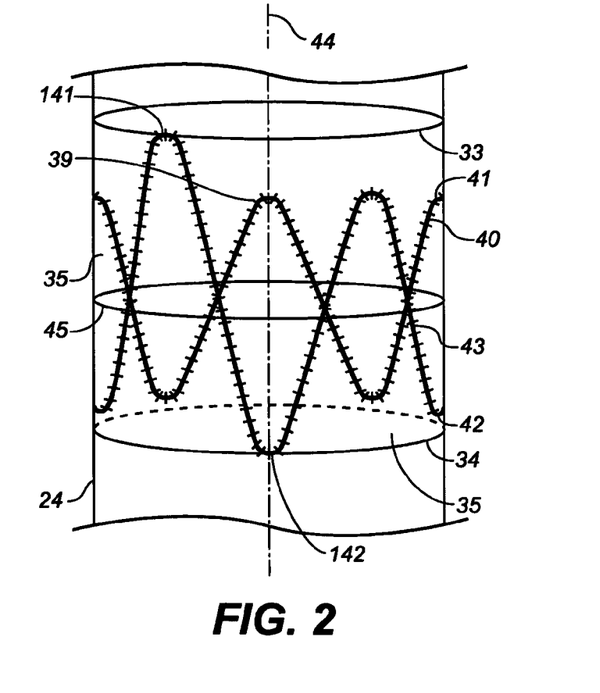
FIG. 2 is a perspective view of the annular support member of FIG. 1 sewn on to graft material forming a tubular member.

As illustrated in FIG. 2, the annular support member 40 is shown attached to tubular graft material 24 of a prosthesis. The longer crest 141 defines an upper circumference 33 generally perpendicular to the central axis 44 and the longer trough 142 defines a lower circumference 34 generally perpendicular to the central axis 44. The upper circumference 33 and lower circumference 34 define a circumferential area (band) 35 of graft material between the longer crest 141 and the longer trough 142 of the annular member 40.

Figure 3:
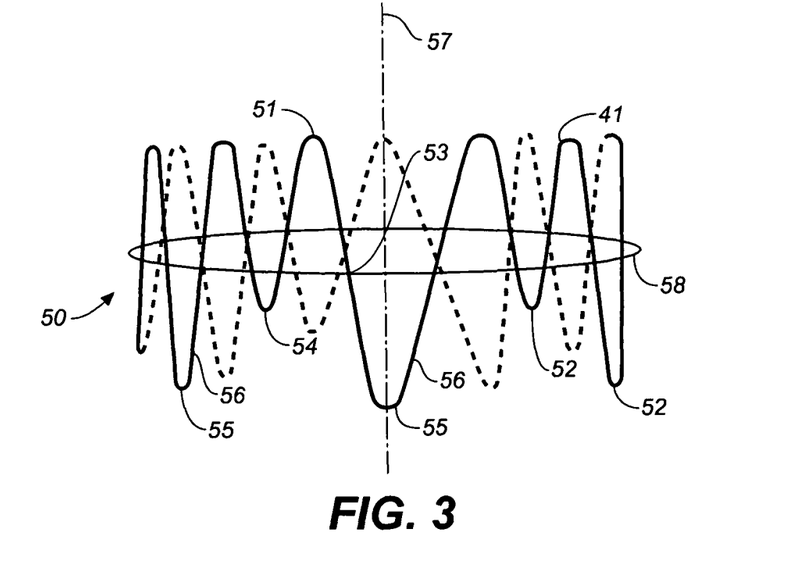
FIG. 3 is an elevational perspective view of a second embodiment of an annular support member of a support structure of an endoluminal prosthesis according to an embodiment of the invention.

FIG. 3 illustrates another embodiment of an annular support member 50 used in the endoluminal prosthesis 20 of an embodiment according to the invention. The annular support member 50 comprises five connected M-shaped portions 56 in a cylindrical undulating ring. In forming this pattern, the annular member 50 comprises straight spokes 53 connected by rounded alternating crests 51 and troughs 52 encircling a central axis 57 to provide a continuous ring. The crests 51 are generally of the same height. The troughs 52 comprise alternating shorter troughs 54 and longer troughs 55 formed so that the longer troughs 55 extend a greater distance axially from the middle circumference 58 (middle between the extremes of crest and trough) of the annular member 50 than the shorter troughs 54.

Figure 4:
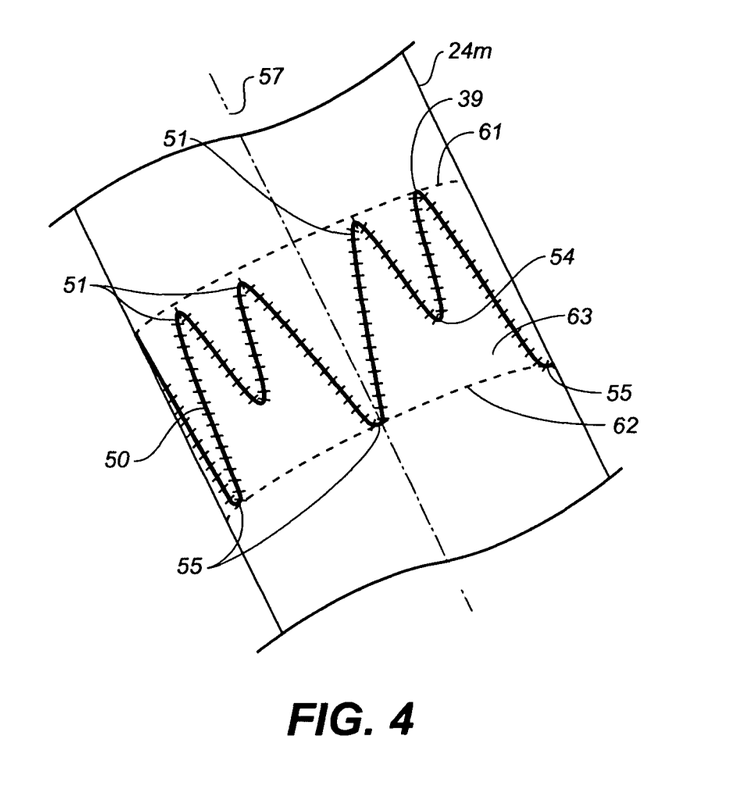
FIG. 4 is a perspective view of the annular support member of FIG. 3 sewn on to graft material forming a tubular member, in particular at the proximal end of such a tubular member.

As illustrated in FIG. 4, the annular support member 50 is shown attached to the tubular graft material 24m. The crests 51 define an upper circumference 61 and the troughs 55 define a lower circumference 62 generally perpendicular to the central axis 57. The upper circumference 61 and lower circumference 62 define a circumferential area (band) 63 of graft material 24m between the crests 51 and the longer trough 55 of the annular member 50.

The annular support members 40, 50 shown in FIGS. 1 and 2, and FIGS. 3 and 4, are preferably a spring members having a predetermined radii and formed of a loop of wire with ends joined together (or a wire ring). Such annular members 40, 50 are preferably constructed of a material such as Nitinol in a superelastic, shape set, annealed condition. After a cylindrical undulating ring is formed with the wire, the ends of the Nitinol wire are joined end to end inside a connection tube by an inline crimp.

FIGS. 5-8B illustrate portions of an endoluminal prosthesis 20 according to the present invention in use as an aneurysm exclusion device. The prosthesis 20 includes a main body portion 25 having an aortic portion 26, a long iliac portion 27, a short iliac portion 28 and an iliac extension 29. The prosthesis 20 is constructed of a graft material 24a formed into a bifurcated tubular member as illustrated. The graft material 24a is preferably a biocompatible, low-porosity woven fabric, such as a woven polyester. The graft material 24a is thin-walled so that is may be compressed into a small diameter catheter, yet capable of acting as a strong, leak-resistant, fluid conduit when expanded to a tubular form.

The prosthesis 20 is further constructed of a plurality of radially compressible support members 38 (including support members 50a-d, 50t and 40a-f) for supporting the graft and/or biasing a proximal end 30 or a distal end 31 of the prosthesis into conforming fixed engagement with an interior surface of aorta 10. The annular support members 40, 50 illustrated in FIGS. 1 and 3 are examples of the many types of support members 38 that may be used in the prosthesis 20. As described below, in this embodiment, the configuration of the annular support members 40 of FIGS. 1 and 2 are used as support members 40a-f in the distal portions of the prosthesis 20 and the configuration of annular support members 50 of FIGS. 3 and 4 are used as support members 50a-d in the proximal end 30 and an aortic portion 26 of the prosthesis 20. In addition, a transition support member 50t is used as a transition member between support members 40a-e, support members 50a-d.

Support members 38 are attached to the graft material 24a with sutures 39 and are preferably constructed of a material such as Nitinol in a superelastic condition. At least a proximal support member 50a biases proximal end 30 of the prosthesis 20 into conforming engagement with the internal wall of the aortic blood vessel to provide a substantial sealing engagement therewith, i.e., a leak resistant seal. Preferably the support structures 38 are spring members, particularly the proximal support structure 50a. In an embodiment according to the invention, the support structures 38 are sewn within graft material 24a using a polyester suture. A preferred stitch pattern may for example, be a locking stitch, e.g., including two generally parallel stitches extending along opposite sides of the wire, and a cross-over stitch around the wire for pulling the parallel stitches together to achieve tight attachment of graft material 24 to the wire spring. In one embodiment, the stitching is used to attach the spring along the entire length of spring wire. In one embodiment, 2-4 stitches per apex are used. The annular support members (40, 50, 40a-f, 50a-d, 50t) are sewn on to the inside or the outside of their respective tubular graft material 24, 24m or 24a. Alternatively, the annular support members (40, 50, 40a-f, 50a-d, 50t) may be enclosed within their respective graft material 24, 24m, or 24a.

As illustrated in FIGS. 5-8B, a central axis 22 generally defines a prosthesis length or a longitudinal direction along the prosthesis. The support structures 38 in the long iliac portion 27 comprise annular members 40a-f constructed in the same manner as annular support member 40 as described above with reference to FIG. 1. The support structures 38 in the aortic portion comprise annular members 50a-d constructed in the same manner as annular support member 50 as described above with reference to FIG. 3 and support member 50t. The support member 50t is a transitional member at the distal portion of the aortic portion 26 and the comprises straight members 53t connected by crests 51t and troughs 52t. The troughs 52t are of the same length along the axis 22, and the crests 51t are of the same length along the axis 22 except for two lateral peaks 54t, one on each side lateral side of the aortic portion 26 of the main body 25.

As shown in FIGS. 5, 6A-F, and 8A, the annular members 40a-f are arranged on the prosthesis 20 so that the protruding apices or longer crests 141a-e of each annular member 40a-e respectively are staggered from the adjacent longer troughs 142b-f of adjacent annular members 40b-f, respectively, in a circumferential direction, while respectively overlapping each other in an axial or longitudinal direction. The annular support members 40a-f, sewn on to the graft 24 with sutures 39, provide columnar support with substantial flexibility in the iliac region to accommodate anatomy which tends to vary from patient to patient and may be extremely tortuous, particularly in highly diseased anatomy. The annular support members (40a-f) are coaxially spaced so that a long trough (141a-f) and a long crest (142a-f) of annular support members immediately adjacent a particular annular support member, extend into a circumferential area defined by such annular member, similar to the limits of the circumferential area 35 defined by annular support member 50 as shown in FIG. 2. The long troughs 142, 142a-f and crests 141, 141 a-f are sewn into the graft 24, in spaces created between the troughs and crests of adjacent annular support members. The close approach spacing of the annular support members and the relatively short length of attached graft material between these closely spaced portions of adjacent support members provide relatively small accommodation for relative longitudinal movement between adjacent support members. The limited flexibility or longitudinal movement provides columnar support between annular support members along the axis of the endoluminal prosthesis. In the embodiment shown, the stresses e.g. the columnar forces, are transmitted along the length of the device between the annular support members, e.g., from an annular support member, to the graft material to which they are attached, and then from the graft material to the adjacent annular support member. Unlike the prior art, there are no axial or lateral connecting elements between adjacent otherwise unconnected annular support members other than the graft material between the annular support members.

Figure 6A:
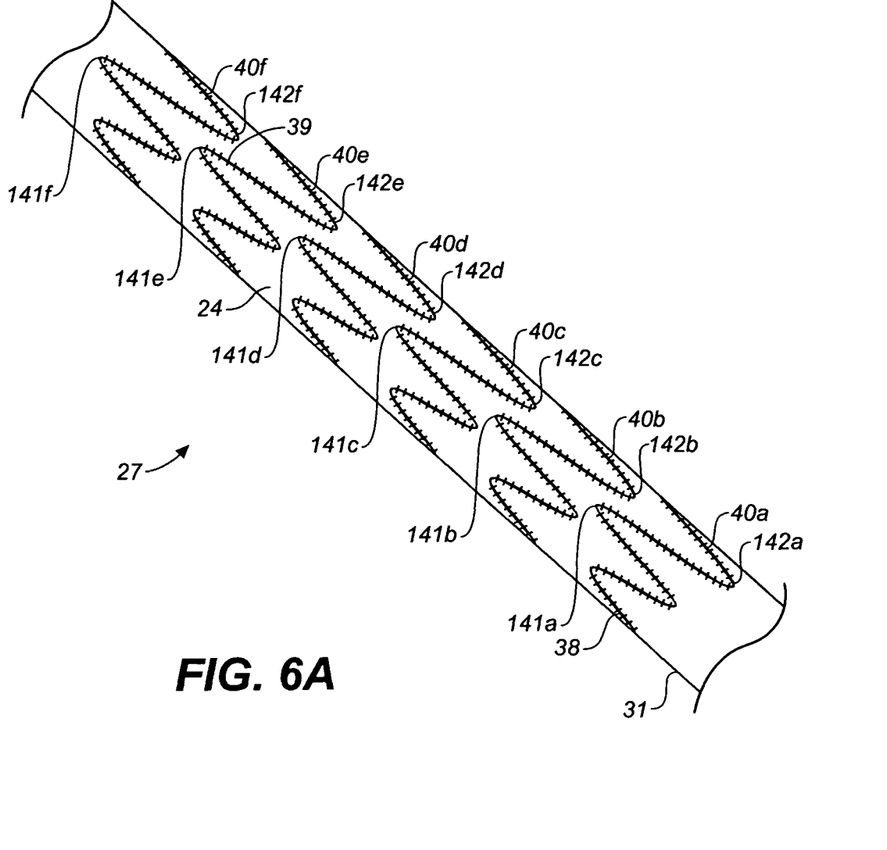
FIG. 6A is an enlarged perspective view of an iliac portion of the prosthesis main body shown in FIG. 5.
Figure 6B:
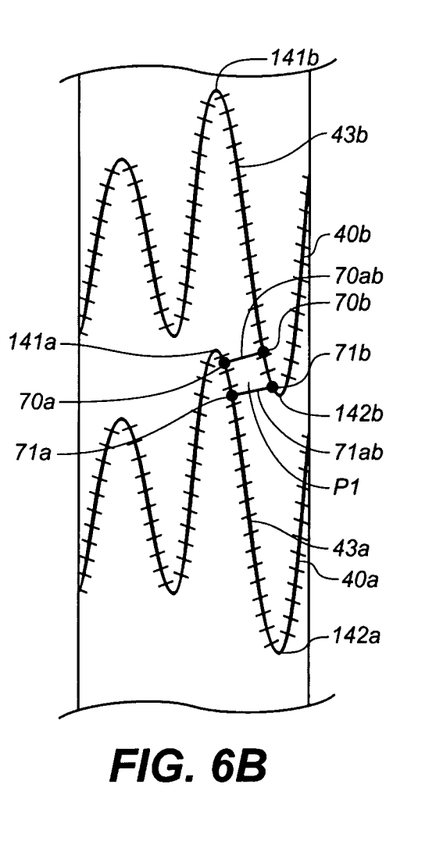
FIG. 6B is an enlarged view of a portion of FIG. 6A.

Referring now to FIGS. 6B-6F an enlarged portion of the long ipsalateral iliac portion limb 27 is illustrated in various positions in which there is some limited axial movement of the support members 40a and 40b with respect to each other. In particular, the spacing of the support members 40a and 40b with respect to each other permits movement of the support members 40a and 40b with respect to each other while the arrangement of the longer peak 141a of support member 40a with respect to the longer trough 142b of support member 40b limits such motion. The longer trough 142b and longer peak 141a are restricted to movement with respect to each other to parallelograms defined by two points selected points on each of the longer through 142b and longer peak 141a where the distance between the two points on the longer trough 142b is equal to the distance between the two points on the longer peak 141a. As illustrated in FIG. 6B, the support members 40a and 40b are in an initial position in which there is no axial or rotational movement of the support members 40a and 40b with respect to each other. The straight spoke 43a joining the longer peak 141a and longer trough 142a of the support member 40a defines two points 70a and 71a on the straight spoke 43a. The straight spoke 43b joining the longer peak 141b and longer trough 142b of the support member 40b defines two points 70b and 71b on the straight spoke 43b. The distance between the points 70a and 71a is equal to the distance between points 70b and 71b. Thus equidistant line segments 70ab and 71ab can be drawn between the point 70a of strut 43a and point 70b of strut 43b, and between the point 71a of strut 43a and point 71b of strut 43b, respectively. Thus, the line segments defined by points 70a and 70b of the strut 43a, and points 71a and 71b of strut 43b, and the line segments 70ab and 71ab define a parallelogram P1.

Figure 6C:
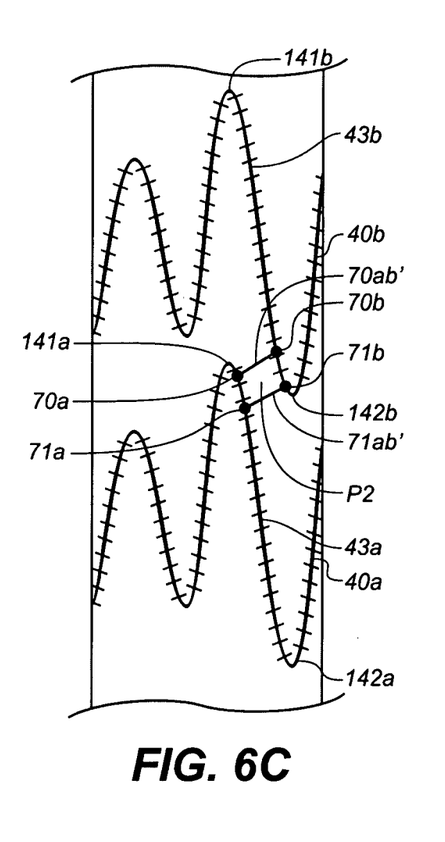
Figure 6D:
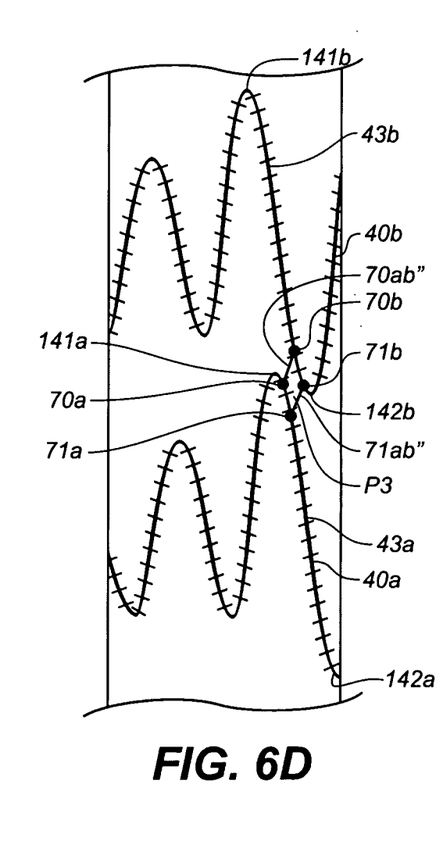

As illustrated in FIG. 6C, the longer peak 141a of the support member 40a is displaced axially away from and rotated with respect to the longer trough 142b of support member 40b. The configuration overlap of the longer trough 142b and longer peak 141a as described above with reference to FIG. 6A, limits the movement of the longer trough 142b and longer peak 141a with respect to one another to a range of movement generally defined by line points 70a, 71a, 70b and 71b. In this figure segments 70ab' and 71ab' segments of struts 43a, 43b defined by points 70a, 71a and 70b, 71b respectively define, a parallelogram P2. As illustrated in FIG. 6D, the longer peak 141a of the support member 40a further displaced axially away from and rotated with respect to the longer trough 142b of support member 40b. The positioning of the longer trough 142b and longer peak 141a with respect to each other is defined by lines 70ab'' and 71ab'' and segments of struts 43a, 43b defined by points 70a, 71a and 70b, 71b respectively forming parallelogram P3.

Figure 6E:
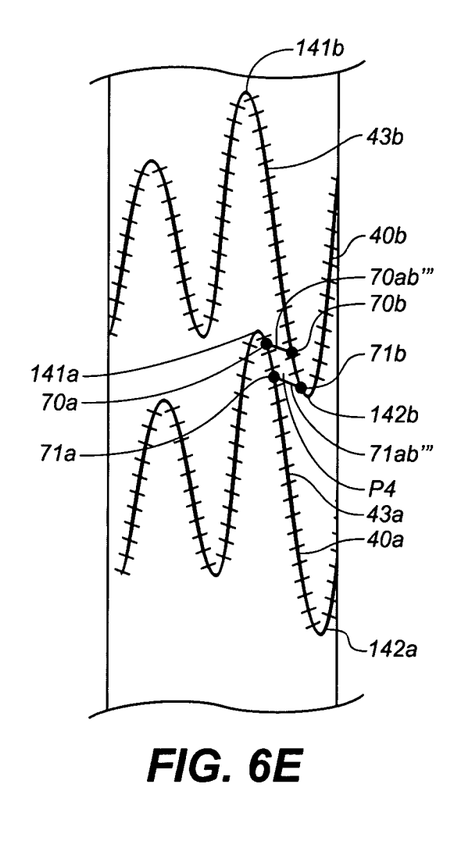
Figure 6F:
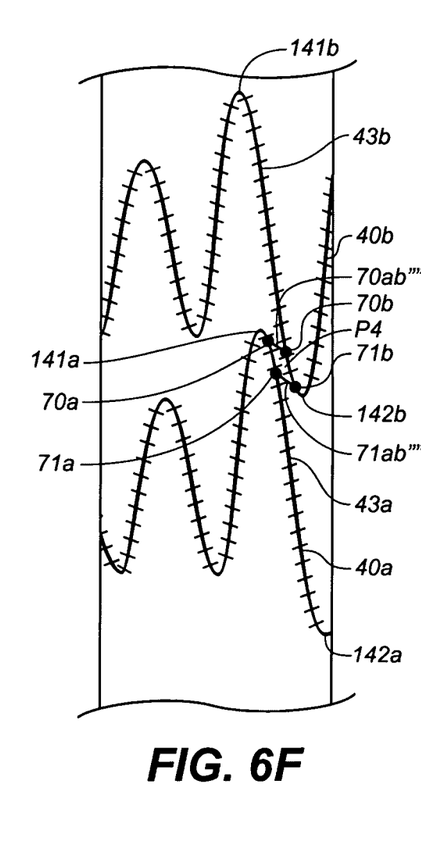

As illustrated in FIG. 6E, the longer peak 141a of the support member 40a is displaced axially toward and rotated with respect to the longer trough 142b of support member 40b. A range of movement is generally defined by line segments 70ab''', 71ab''' and segments of struts 43a, 43b defined by points 70a, 71a and 70b, 71b respectively, which form a parallelogram P4. As illustrated in FIG. 6F, the longer peak 141a of the support member 40a further displaced axially toward and rotated with respect to the longer trough 142b of support member 40b. The positioning of the longer trough 142b and longer peak 141a with respect to each other is defined by lines 70ab'''' and 71ab'''' and segments of struts 43a, 43b defined by points 70a, 71a and 70b, 71b respectively, forming parallelogram P5. Accordingly, unlike many stent grafts of the prior art, a connecting element in addition to the support provided by annular members sewn on to a tubular graft, is not required.

Figure 5:
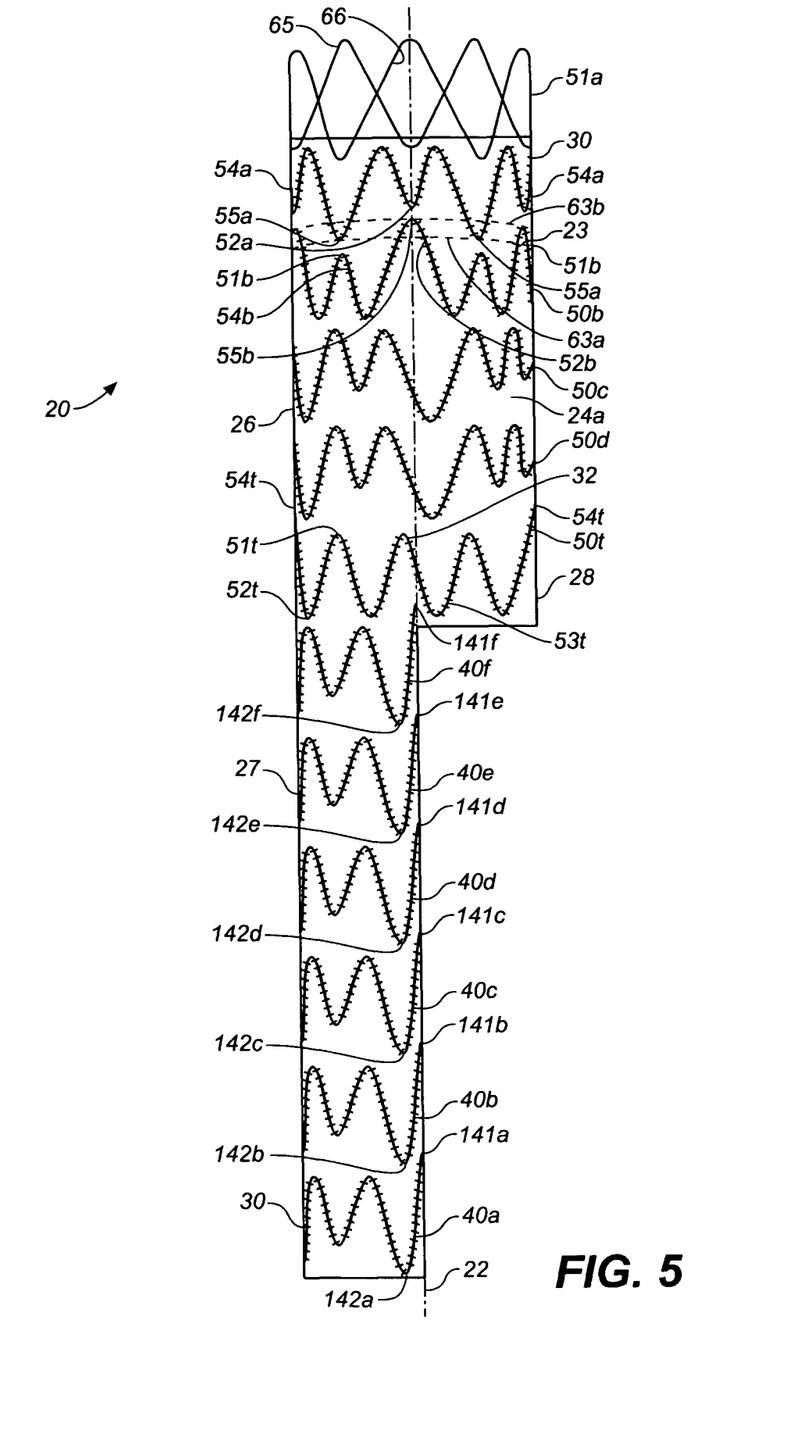
FIG. 5 is an elevational view showing a bifurcated graft main body in an expanded condition using a plurality of annular support members illustrated in FIGS. 1 and 3.
Figure 7:
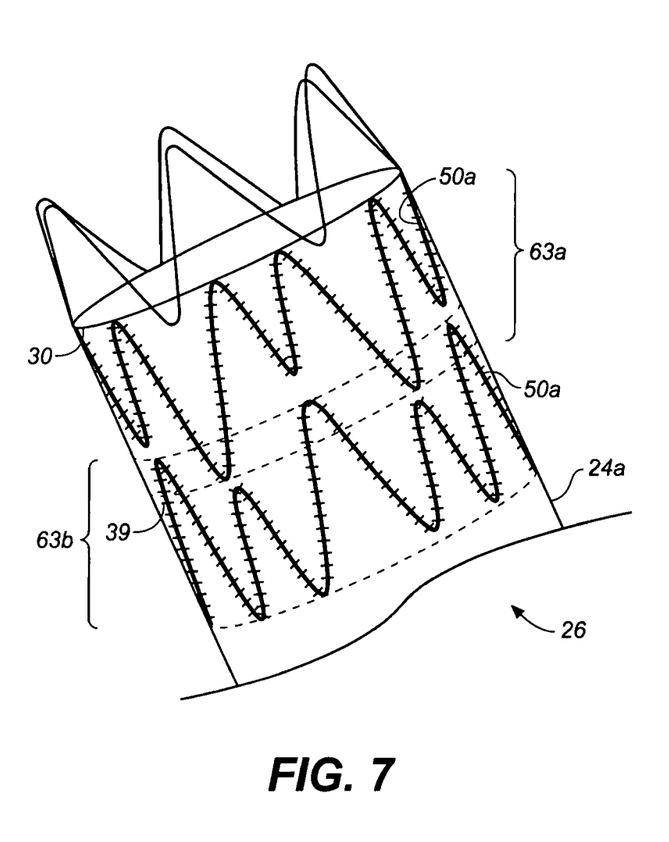
FIG. 7 is an enlarged perspective view of the proximal portion of the prosthesis main body shown in FIG. 5
Figure 8A:
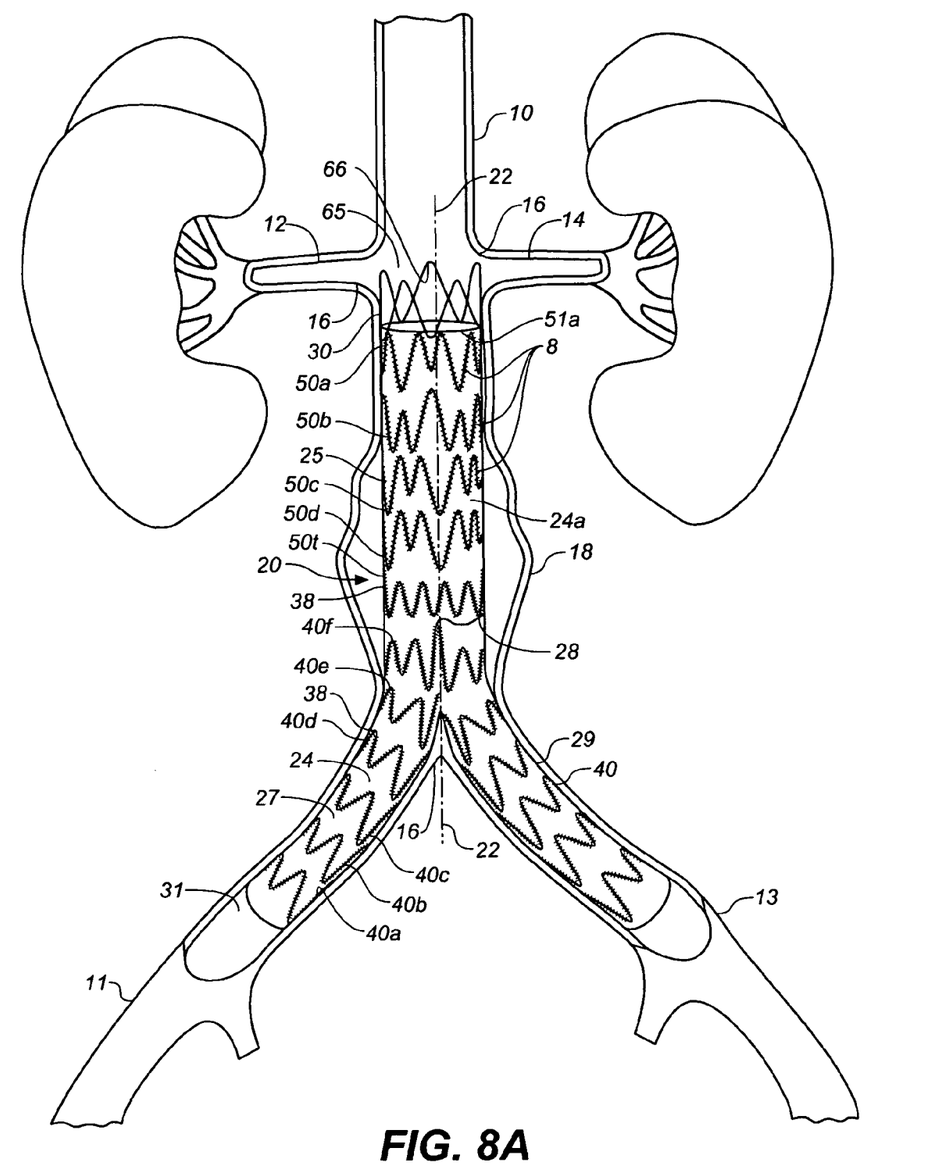
FIG. 8A is an elevational, partial cutaway view showing the bifurcated graft main body shown in FIG. 4 with an iliac extension fully deployed within an aorta and lateral iliac vessels of a patient having an abdominal aortic aneurysm.

As shown in FIGS. 5, 7 and 8A, the annular support members 50a-d and 50t are sewn on to the graft 24 with sutures 39 in a manner that provides columnar support with substantial flexibility in the aortic region. The proximal support member 50a is sewn on the proximal end 30 of the prosthesis 20 with crests 51a sewn onto edge of the graft material 24 and longer troughs 55a (FIG. 5) extending a greater distance along the length of the of the prosthesis than the shorter troughs 54a. The troughs 52a (54a and 55a) are thus located at different levels along the prosthesis length and thereby provide radial sealing force at different levels to provide greater conforming sealing engagement with the aorta wall along the length of the prosthesis proximal end 30. An adjacent support member 50b is oppositely oriented from the support member 50a, i.e., so that the M-shaped patterns are upside down. As such, the crests of the annular member 50 become troughs and the troughs become crests (i.e., the crests being toward the proximal end 30). The crests 52b extend in a proximal direction with alternating shorter crests 54b and longer crests 55b adjacent the proximal support member 50a. The shorter crests 54b of support member 50b are aligned with the longer troughs 55a of support member 50a. The longer crests 55b of the support member 50b are aligned with the shorter troughs 54a of the support member 50a. Longer crests 55b extend into and are attached within a circumferential area 63a defined by support member 50a while longer troughs 55a of support member 50a extend into and are attached within a circumferential area 63b defined by support member 50b. Support members 50c and 50d are similarly affixed to the graft 24a. Support member 50t is initially in an oval shape prior to being sewn on to the graft 24a with the long axis of the oval shape from the anterior to posterior of the prosthesis 20 (FIG. 5 showing an anterior view of the prosthesis 20). The longer peaks 54t extend into the region of the graft 24a defined by the adjacent support member 50d, to provide columnar support between the annular support members 50d and 50t.

Figure 8B:
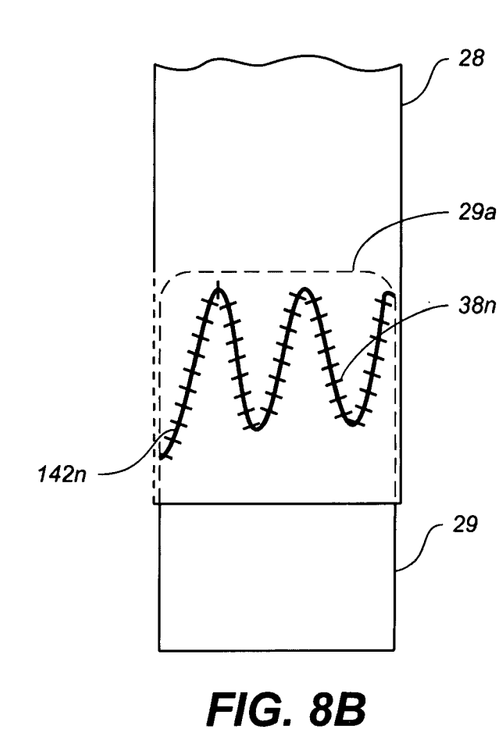
FIG. 8B is an enlarged elevational view of a portion of the prosthesis in FIG. 8A illustrating the connection of the iliac extension to the short leg of the main body in which the proximal support structure of the extension is shown in phantom.

Referring to FIG. 8A, the prosthesis 20 is shown in place in an abdominal aorta 10. The aorta 10 is joined by renal arteries 12 and 14 at the aorto-renal junction 16. Just below the aorta-renal junction 16 is an aneurysm 18, a diseased region where the vessel wall is weakened and expanded. Below the aneurysm 18, the aorta bifurcates into right and left iliac vessels 11, 13, respectively. The elongated bifurcated tubular prosthesis 20 is deployed at the region of aneurysm 18 for the purpose of relieving blood pressure against the weakened vessel wall, by acting as a fluid conduit through the region of the aneurysm 18. In its deployed condition, prosthesis 20 defines a central longitudinal axis 22 extending in a direction of blood flow through aorta 10, which generally defines the length or a longitudinal direction with respect to the prosthesis 20. Proximal annular support member 50a is designed to exert a radially outward force sufficient to bias graft material 24 of the endoluminal prosthesis 20 into conforming fixed engagement with the interior surface of aorta 10 above aneurysm 18 and to provide a leak resistant seal between the prosthesis and the inner wall of the aorta 10. The other annular support members may also provide radially outward forces that help seal the proximal end 30 against the wall of the aorta 10. The proximal aortic portion 26 of the prosthesis 20 is located within aorta 10, and is joined to the long ipsalateral iliac portion limb 27 which is to be located within the right iliac vessel 11. A separate single contralateral extension limb 29 is constructed in a manner similar to the long iliac limb portion 27 using annular support members (e.g., 40), e.g., sewn into graft material 24. After deployment of the main body portion 25, the contralateral extension limb 29 is located within left iliac vessel 13, and near the graft leg junction 32 within the short iliac portion 28. As illustrated in FIG. 8B, the proximal end 29a of the contralateral extension limb 29 includes a proximal support member 38n (shown in phantom) biasing the proximal end 29a into conforming fixed engagement with the interior surface of the short iliac portion 28. The proximal support member 38n includes longer trough 142n, but does not include a longer crest.

In the main body portion 25 an open spring 65 is sewn on to the graft material 24 at the proximal end 30 providing uncovered portions or open spring areas 66 beyond the proximal end of the graft material 24. Thus the open spring 65 may be deployed over the renal arteries 12, 14, without blocking the blood flow through arteries 12, 14. Thus the prosthesis 20 may be situated with proximal end 30 relatively close to aorto-renal junction since openings 66 may be aligned with renal arteries 12 and 14 so as not to block blood flow. To deploy the prosthesis 20, the main body portion 25 of the prosthesis may be loaded into a catheter. Support members 38 are radially compressed to facilitate loading insertion of prosthesis 20 within a sheath of a catheter. The main body portion 25 is delivered in a compressed state via catheter through a surgically accessed femoral artery, to the desired deployment site. The main body portion 25 is deployed wherein the support members expand or are expanded into the deployed configuration illustrated in FIGS. 5 and 8A-8B.

Using a second catheter, the contralateral limb 29 may be separately deployed through a surgically accessed femoral artery after placement of the main body portion 25. These and suitable delivery methods and apparatus are generally known in the art and may be used to deliver the prosthesis. This may be done one of several ways. A surgical cut down may be made to access a femoral iliac artery. The catheter is then inserted into the artery and guided to the aneurysm site using fluoroscopic imaging where the device is released from the catheter. Where expandable members are used, the members supporting the graft, biased in a radially outward direction, then expand to engage the prosthesis in the vessel against the vessel wall to provide an artificial lumen for the flow of blood. Another technique includes percutaneously accessing the blood vessel for catheter delivery, i.e., without a surgical cutdown. An example of such a technique is set forth in U.S. Pat. No. 5,713,917, incorporated herein by reference.

Another embodiment according to the invention provides a method of manufacturing an endoluminal prosthesis. In the method a tubular graft constructed of a graft material is provided. The tubular graft defines an opening with an axis therethrough. The method further includes attaching a first annular support member to the graft material, the first annular support member comprising a plurality of first apices extending in a first axial direction with respect to the axis of the tubular graft, wherein at least one of the plurality of first apices extends axially beyond another of the plurality of first apices. The method also includes attaching a second annular support member to the tubular graft adjacent the first annular support member, the second annular support member comprising a plurality of second apices extending in a second axial direction opposite to the first axial direction, at least one of the second apices of the second annular support member defining a circumferential area of a portion of the tubular graft around the second annular support member, wherein the at least one of the plurality of first apices of the first annular support member is attached to the tubular graft within the circumferential area.

Another embodiment according to the invention provides another method of manufacturing an endoluminal prosthesis. In the method a tubular graft constructed of a graft material is provided. The tubular graft defines an opening with an axis therethrough. The method further includes attaching a first annular support member to the graft material, the first annular support member comprising a plurality of apices coupled by a plurality of spokes and forming a closed ring defining a circumference, wherein the apices comprise alternating crests and troughs, wherein at least one of the troughs extends axially beyond an other of the troughs and wherein the troughs of the annular support member comprise a plurality of alternating longer troughs and shorter troughs. A second annular support member is attached to the tubular graft adjacent the first annular support member, the second annular support member comprising a plurality of second spokes coupled by a plurality of second apices to form a second ring, wherein the second annular support member is attached to the graft material to define a circumferential area of the graft material around the second annular support member. Finally, one of the longer troughs of the first support member is attached to the graft material within the circumferential area of the second support member. Another aspect of this method may provide alternating second crests and second troughs of the plurality of second apices of the second annular support member, wherein the second crests comprise a plurality of alternating longer crests and shorter crests. According to this further aspect, the method may include attaching the longer troughs of the first annular support member substantially in longitudinal alignment with the shorter crests of the second annular support member; and attaching the shorter troughs of the first annular support member in substantially longitudinally aligned with the longer crests of the second annular support member. This method may also further include attaching the first annular support member to the graft material to define a circumferential area of the graft material around the first annular support member; attaching the longer crests of the of the second support member within the circumferential area of graft material around the first annular support member; and attaching the longer troughs of the first support member within the circumferential area of graft material around the second annular support member.

Although this detailed description sets forth particular embodiments according to the invention, the present invention contemplates various other vascular grafts or endoluminal prostheses, especially those in which a combination of columnar support, flexibility and/or improved sealing is desired. For example configurations according to the present invention may be used with forcibly expanded coronary and peripheral stents or stent-grafts, covered grafts, vascular grafts, and other aneurysm exclusion devices. The expandable support structures on various embodiments of the devices may be, for example, self-expanding, balloon expandable, or otherwise forcibly expanded.

While the invention has been described with reference to particular embodiments, it will be understood to one skilled in the art that variations and modifications may be made in form and detail without departing from the spirit and scope of the invention.

What is claimed is:
1. An endoluminal prosthesis comprising:
   a tubular graft comprising a graft material, a proximal portion having a proximal opening, and a distal portion having a distal opening, the proximal and distal openings and the graft material forming a lumen for the flow of body fluid therethrough; and
   a first annular support member comprising a plurality of spokes coupled by a plurality of apices to form a closed ring, having an axis extending longitudinally therethrough,
   a second annular support member comprising a plurality of spokes coupled by a plurality of apices to form a closed ring, having an axis extending longitudinally therethrough, said first and second annular support members being attached to said tubular graft, but otherwise unconnected to one another,
   wherein each of the annular support members are attached to the graft material along the tubular graft to define, for each of the plurality of annular support members, a corresponding circumferential area of the graft material around a corresponding annular support member,
   wherein at least one of the apices of said first annular support member is attached within the corresponding circumferential area of the graft material of said second annular support member, which is adjacent the first annular support member, so that at least one of the apices of said first annular support member extends axially toward said second support member and axially beyond one of said apices of said second annular support member, and wherein at least one of the apices of the first annular support member extends axially beyond an other of the apices of the first annular support member.

2. The endoluminal prosthesis of claim 1 wherein the apices of each support member comprising alternating crests and troughs.

3. The endoluminal prosthesis of claim 2
wherein each of the apices extending beyond the other of the apices of the annular support members is attached to the graft material within the corresponding circumferential area of an adjacent support member.

4. The endoluminal prosthesis of claim 3 wherein the tubular graft has a length and each of the apices extending beyond the other of the apices are substantially aligned with each other along the length of the tubular graft.

5. The endoluminal prosthesis of claim 3 wherein each of the said apices extending beyond the other of the apices is a crest extending axially beyond the other of the crests of a corresponding support member.

6. The endoluminal prosthesis of claim 3 wherein each of the said apices extending beyond the other of the apices is a trough extending axially beyond the other of the troughs of a corresponding support member.

7. The endoluminal prosthesis of claim 1 wherein at least one of the annular support members comprises a spring biased in a radially outward direction.

8. The endoluminal prosthesis of claim 7 wherein the spring is arranged to form a sealing relationship between the tubular graft and the inner wall of a body lumen.

9. The endoluminal prosthesis of claim 1 wherein the at least one of the apices is attached to the graft material by a stitch.

10. The endoluminal prosthesis of claim 9 wherein the stitch comprises at least between 2-4 stitches per said at least one of the apices.

11. The endoluminal prosthesis of claim 2 wherein the apices of the crests in one of said annular members are circumferentially aligned with one another.

12. An endoluminal prosthesis comprising:
a tubular graft comprising a graft material and having a length, a proximal portion having a proximal opening and a proximal end, and a distal portion having a distal opening and a distal end, the proximal and distal openings and the graft material forming a lumen along the length for the flow of body fluid therethrough; and
a plurality of annular support structures, each support structure comprising a series of undulating members and defining a circumference and crests extending toward said proximal end and troughs extending toward said distal end, said support structures being attached to said tubular graft, but otherwise being unconnected to one another,
wherein at least one undulating member of a support structure lengthwise overlaps an undulating member of an adjacent support structure and is offset from the undulating member of the adjacent support structure about the circumference of the adjacent support structure such that crests from one annular support member are substantially aligned with troughs of an adjacent annular support member.

13. The endoluminal prosthesis of claim 12 wherein when said prosthesis is in a straight condition at least one undulating member of a support structure lengthwise overlaps an undulating member of an adjacent support structure and is offset from the undulating member of the adjacent support structure about the circumference of the adjacent support structure such that crests from one annular support member are substantially aligned with troughs of an adjacent annular support member.

14. The endoluminal prosthesis of claim 12 wherein the apices of the crests in one of said annular members are circumferentially aligned with one another.

15. An endoluminal prosthesis comprising:
a tubular graft comprising a graft material, a proximal portion having a proximal opening, and a distal portion having a distal opening, the proximal and distal openings and the graft material forming a lumen for the flow of body fluids therethrough;
a first annular support member, comprising a plurality of spokes coupled by a plurality of apices to form a closed ring having an axis extending longitudinally therethrough, the apices comprising alternating crests and troughs, wherein one of the apices extends axially beyond an other of the apices,
wherein the first annular support member is attached to the graft material, but otherwise unconnected to another support member,
further comprising a second annular support member comprising a plurality of second spokes coupled by a plurality of second apices to form a second ring,
wherein the second annular support member is attached to the graft material to define a circumferential area of the graft material around the second annular support member, and
wherein the one of the apices extending beyond an other of the apices of the first support member is attached to the graft material within the circumferential area of the second support member,
wherein the alternating troughs of the first annular support member comprise a plurality of alternating longer troughs and shorter troughs, and
wherein the plurality of second apices of the second annular support member comprise alternating second crests and second troughs and wherein the second crests comprise a plurality of alternating longer crests and shorter crests.

16. The endoluminal prosthesis of claim 15 wherein the longer troughs of the first annular support member are aligned with the shorter crests of the second annular support member and the shorter troughs of the first annular support member are aligned with the longer crests of the second annular support member.

17. The endoluminal prosthesis of claim 16 wherein the first annular support member is attached to the graft material to define a circumferential area of the graft material around the first annular support member, and
wherein the longer crests of the second support member are attached within the circumferential area of graft material around the first annular support member and the longer troughs of the of the first support member are attached within the circumferential area of graft material around the second annular support member.

* * * * *

UNITED STATES PATENT AND TRADEMARK OFFICE
CERTIFICATE OF CORRECTION

| | | |
|---|---|---|
| PATENT NO. | : 8,702,787 B2 | Page 1 of 1 |
| APPLICATION NO. | : 11/218917 | |
| DATED | : April 22, 2014 | |
| INVENTOR(S) | : Samuel Arbefeuille | |

It is certified that error appears in the above-identified patent and that said Letters Patent is hereby corrected as shown below:

In the Specification

In column 14, line 60
"troughs of the of the first support member" should read -- "troughs of the of support member" --

Signed and Sealed this
Fourteenth Day of July, 2015

Michelle K. Lee
*Director of the United States Patent and Trademark Office*